United States Patent [19]
Jakubowicz et al.

[11] Patent Number: 5,360,597
[45] Date of Patent: Nov. 1, 1994

[54] RIBBED MECHANISM FOR MIXING SAMPLE BY VIBRATION

[75] Inventors: Raymond F. Jakubowicz, Rush; Johannes J. Porte, Webster, both of N.Y.

[73] Assignee: Eastman Kodak Company, Rochester, N.Y.

[21] Appl. No.: 34,040

[22] Filed: Mar. 22, 1993

[51] Int. Cl.⁵ ............................................. G01N 35/06
[52] U.S. Cl. ................................... 422/64; 422/63; 422/65; 422/67; 422/68.1; 436/43; 436/47; 436/48; 435/316
[58] Field of Search .............. 422/63, 64, 100, 102, 422/62, 65, 67, 68.1; 436/43, 47, 48; 435/316, 809

[56] References Cited

U.S. PATENT DOCUMENTS

| | | | |
|---|---|---|---|
| Re. 23,634 | 3/1953 | Hewson | 422/67 |
| 3,767,364 | 10/1993 | Ritchie et al. | 422/64 X |
| 3,784,826 | 1/1974 | Bagshawe et al. | 250/106 |
| 3,951,608 | 4/1976 | Trod | 23/259 |
| 3,963,349 | 6/1976 | Albright et al. | 422/64 X |
| 3,971,630 | 7/1976 | Sandrock et al. | 422/64 X |
| 4,341,736 | 7/1982 | Drbal et al. | 422/100 |
| 4,475,411 | 10/1984 | Wellerfors | 422/64 X |
| 5,066,135 | 11/1991 | Meyer et al. | 422/64 X |
| 5,071,625 | 10/1991 | Kelln et al. | 422/72 |
| 5,128,103 | 7/1992 | Wang et al. | 422/64 |
| 5,183,638 | 2/1993 | Wakatake | 422/64 |
| 5,186,709 | 2/1993 | Hissung | 422/64 X |
| 5,186,896 | 2/1993 | Bouchee et al. | 422/72 |
| 5,244,633 | 9/1993 | Jakubowicz et al. | 422/64 |

FOREIGN PATENT DOCUMENTS 0329183 8/1989 European Pat. Off. ...... G01N 35/02
3839080 11/1988 Germany.

*Primary Examiner*—James C. Housel
*Assistant Examiner*—Harold Y. Pyon
*Attorney, Agent, or Firm*—Dana M. Schmidt

[57] ABSTRACT

Apparatus for mixing are disclosed for use in an analyzer providing wet assays in a cuvette. Preferably, they comprise protrusions that project into the path of the cuvette as it passes through preferably the incubator. The protrusions can be fixed or driven, and can project upwardly or sideways into the path of the moving cuvette. The mixing is useful to cause thorough mixing of, e.g., a diluent with a liquid sample.

10 Claims, 12 Drawing Sheets

FIG.9
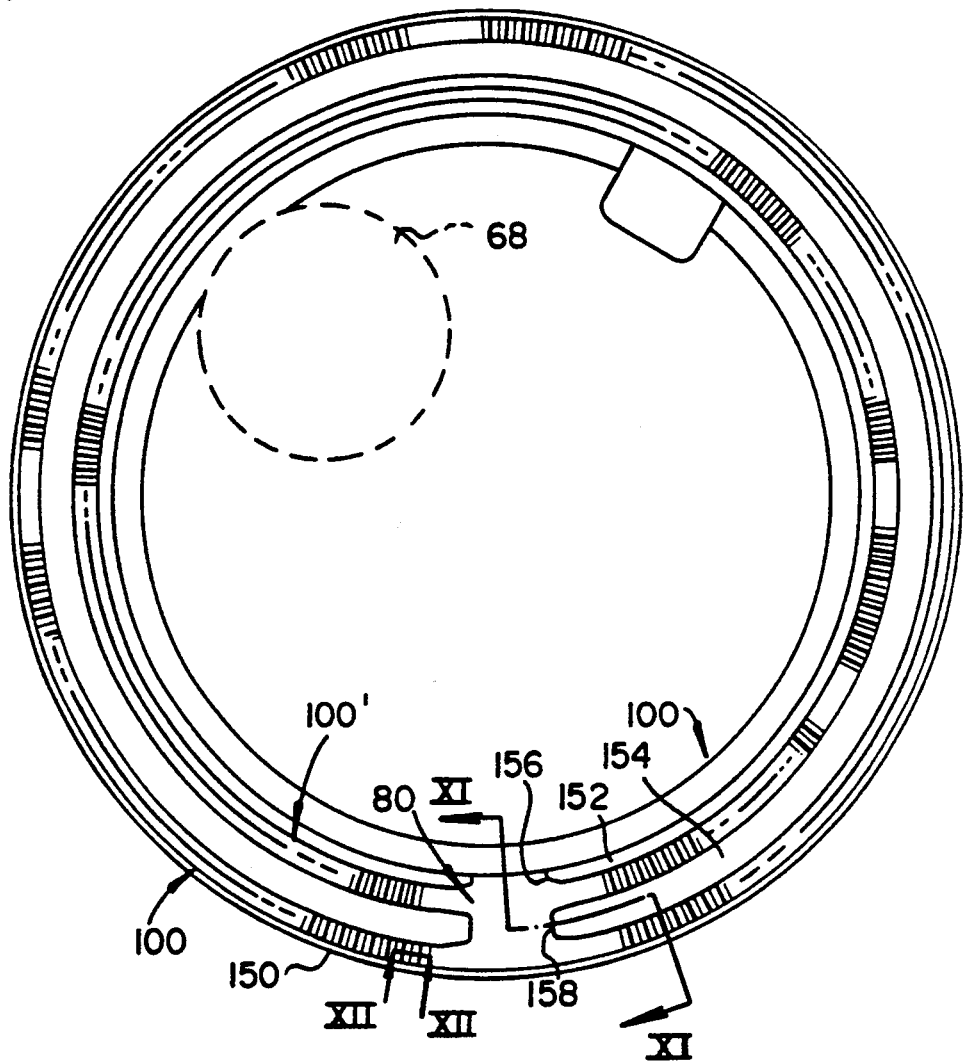
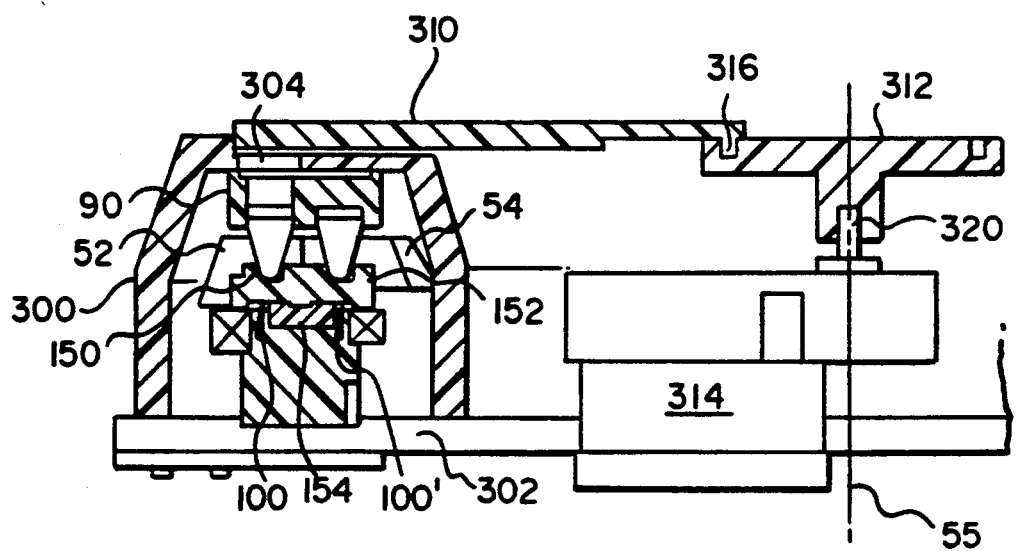
FIG. 17

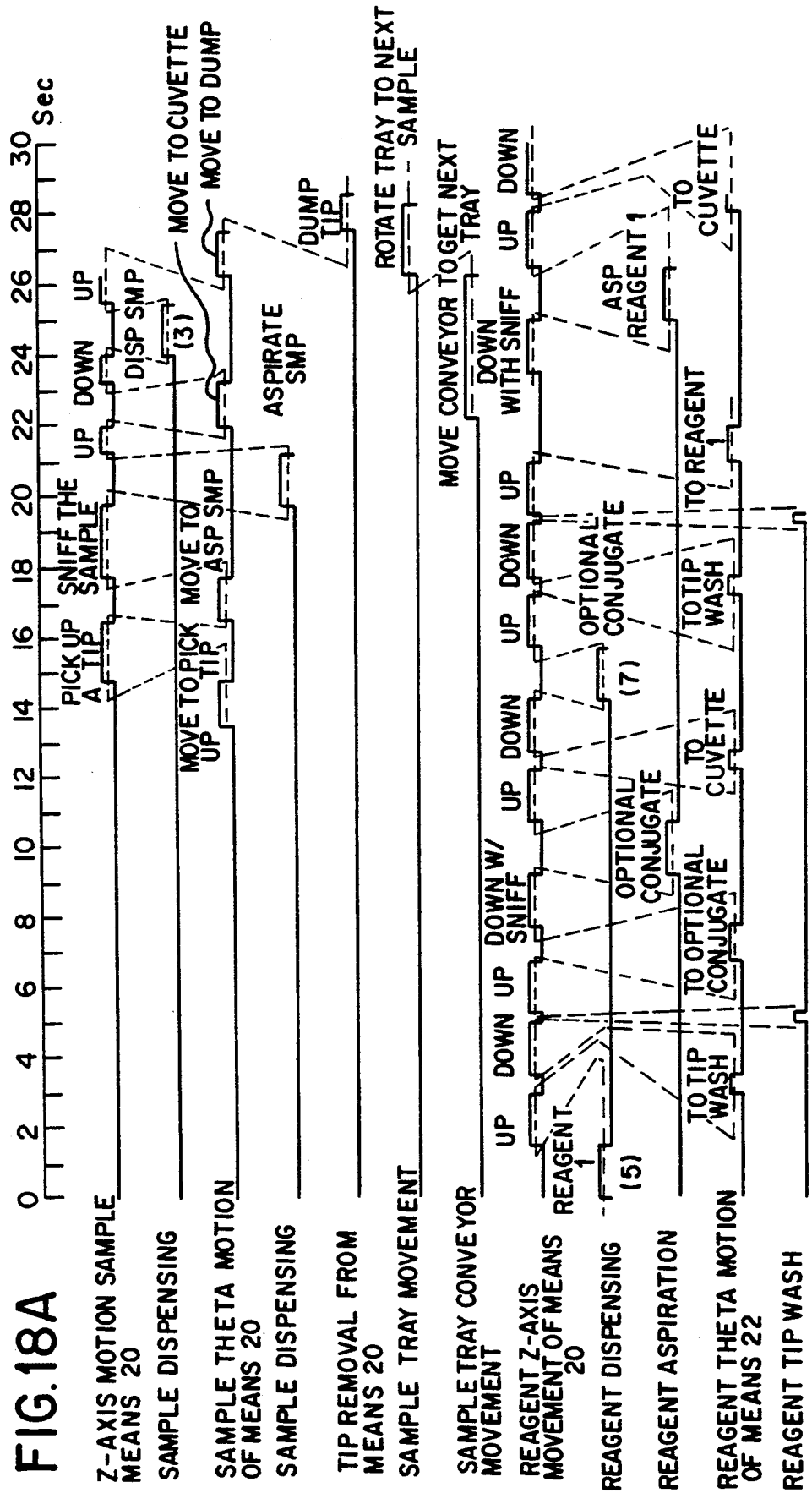

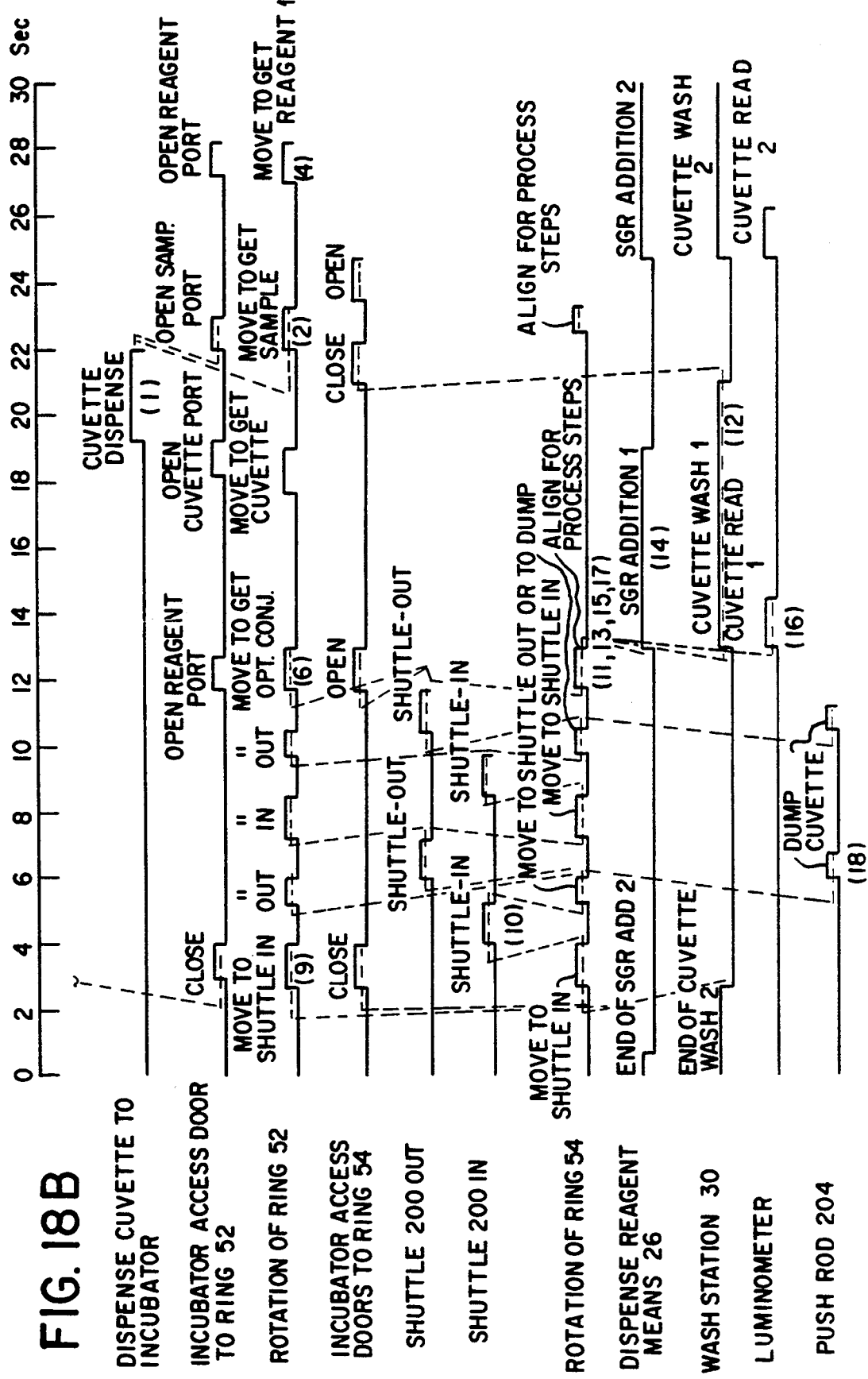

RIBBED MECHANISM FOR MIXING SAMPLE BY VIBRATION

FIELD OF THE INVENTION

This invention relates to an analyzer for assaying analytes in a liquid sample, particularly using wet assays requiring liquid mixing of sample and reagent.

BACKGROUND OF THE INVENTION

In clinical analyzers that do wet assays, it is well known to mount the reaction cuvettes on a rotating platform that carries them from station to station, at least one of those stations being one which causes mixing within the cuvette. Such for example is shown in German OLS 3,839,080, in which cuvettes 301 are apparently vibrated, p. 7, p. 9–10, and p. 19, of the English translation, to cause mixing of the reaction cuvettes, by a mechanism described as providing a "high rate <frequency> and low amplitude", p. 7, for a few seconds, p. 9. It is not clear what those relative terms might mean.

Such a disclosure is inadequate to teach a satisfactory mixing mechanism. The details that are provided are those on p. 19 and FIG. 11, so that it is clear the entire reaction table 302 is vibrated or shaken. Yet, as shown, that table is a fairly massive plate, so that large amounts of energy are required to vibrate the entire plate at some "high" frequency. This large amount of energy is undesired, and isolation of the table is required so that this vibration does not transfer to the rest of the analyzer. Still further, the researcher is left unaware of what high frequencies and low amplitudes are useful. Finally, when adding certain liquids to another liquid, it can be easily shown that merely shaking the cuvette "for a few seconds" is not likely to cause adequate mixing. There is a particular need to provide adequate mixing when adding a diluent to a liquid sample, such as is often done to allow the assay of an out-lier that has a concentration so high as to be otherwise out-of-range.

Other teachings in the art concerning the mixing of liquid within liquid refer to shaking by oscillating the cuvette forward and backward, to cause as it were a "sloshing" of the liquid. Such a system is used in, e.g., the "Amerlite" analyzer. This also is of limited utility, since vigorous sloshing, while causing desired mixing, also causes a loss of liquid from the cuvettes. Gentle sloshing, while effective to retain the liquid in the cuvette, is slow to cause mixing. That is, 60 minutes or more are required to mix by sloshing gently.

Therefore, there has been a problem with prior art wet assay analyzers in that they do not provide rapid mixing of liquid within liquid, without sloshing liquid out of the open cuvettes.

RELATED APPLICATIONS

Commonly owned U.S. Ser. No. 887,990, filed on May 22, 1992, now U.S. Pat. No. 5,244,633, entitled "Analyzer Incubator with Plural Independently Driven Rings Supporting Cuvettes" describes but does not claim mixing means of the type claimed herein.

SUMMARY OF THE INVENTION

The above problem has been solved with an improved mixing apparatus in an analyzer.

More specifically, there is provided an analyzer for conducting a wet assay in a liquid in a cuvette, the analyzer comprising first station means for adding a liquid reagent to a liquid in a cuvette, second station means for mixing the reagent with the liquid already within the cuvette, and station-to-station means for moving cuvettes from station to station along a path. The analyzer is improved in that the mixing means comprise at least one set of spaced-apart protrusions projecting out into said path traced by the cuvettes, the moving means providing relative motion between said protrusions and at least one of said cuvettes, so that the at least one cuvette is repeatedly disturbed by said protrusions and the liquid content is mixed.

Accordingly, it is an advantageous feature of the invention that an analyzer is provided with an improved mixer that more rapidly mixes two liquids in a cuvette than was previously possible by such mixers.

It is a related advantageous feature that such mixing occurs without large expenditure of energy required, for example, to vibrate the entire cuvette support.

Other advantageous features will become apparent upon reference to the following detailed "description" when read in light of the attached drawings.

BRIEF DESCRIPTION OF THE DRAWINGS

FIG. 9 is a plan view of a preferred form of the fixed track that provides the mixer of the invention;

FIG. 17 is a sectioned, fragmentary elevational view of the cover of the incubator and access to the incubator for the processing stations;

FIGS. 18A and 18B are timing diagrams showing representative timing of the operations provided by the incubator of the invention;

DESCRIPTION OF THE PREFERRED EMBODIMENTS

The invention is described by reference to preferred embodiments, wherein wet assay cuvettes are supported in one or more annular supports in an analyzer, that cooperate with each other to cause at least one reaction between a reagent and a sample analyte. In addition, the invention is useful whether the supports are annular or linear, or are plural in number or not, and it is useful also for any mixing, whether or not a sample analyte is to be detected.

As used herein, "complete mixing" means, when the contents to be mixed are of different colors and are scanned by the operator after mixing, that the color is uniform and no color differentiation can be seen in the entire volume that would indicate incomplete mixing. Complete mixing is particularly important when a diluent is being added to the sample.

The Analyzer

Figure 1:
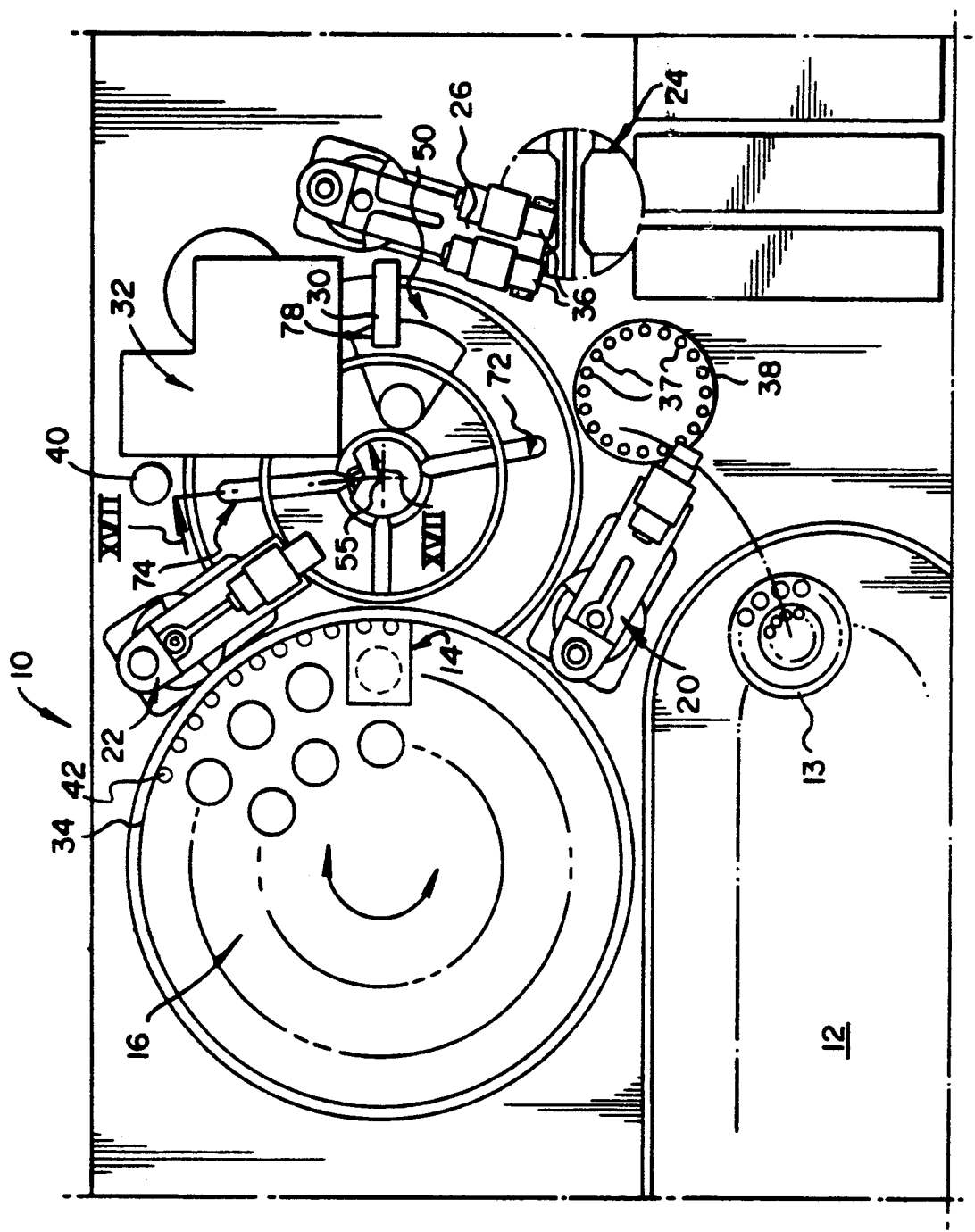
FIG. 1 is a schematic, broken away plan view of an analyzer incorporating the mixing feature of the invention in the incubator.
Figure 2:
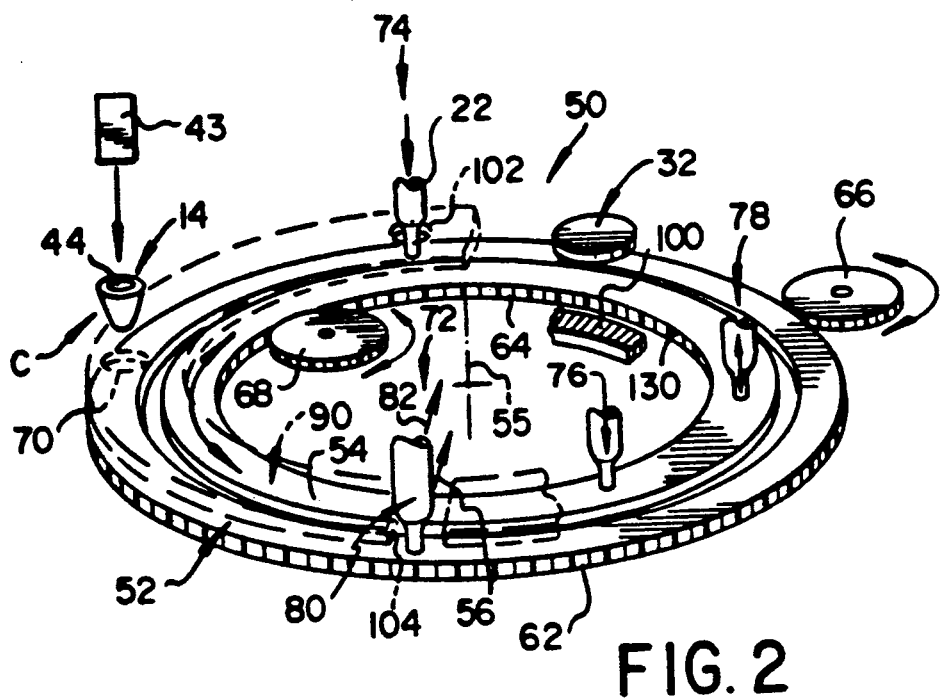
FIG. 2 is a schematic isometric view of the incubator per se and some processing stations associated therewith.

As shown in FIG. 1, the mixer of the invention is constructed for use in an incubator 50 in an analyzer 10 comprising a sample supply station 12, a cuvette supply station 14, FIG. 2, a reagent supply station 16, FIG. 1, means 20 and 22 for transferring sample and reagent to a cuvette disposed in an outer ring of incubator 50, signal reagent supply station 24, means 26 for transferring signal reagent to the cuvette in an inner ring of incubator 50, cuvette wash station 30, and luminometer 32. Except for the incubator and the location of the stations for reagent addition described hereinafter, any suitable construction, including conventional devices, can be used for the sample supply station 12, cuvette supply station 14, reagent supply station 16, transfer means 20, 22 and 26, signal reagent supply station 24, wash dispenser 30, and luminometer 32. For example, the following features are considered to be conventional: supply station 12 includes a position having a device 13 therein that is aligned for sample transfer. (Useful devices 13 include those described and claimed in commonly owned, pending U.S. application Ser. No. 859,780 filed on Mar. 30, 1992, now abandoned by Tomasso et al, entitled "Tray and Magnetic Conveyor".) Supply station 16 includes a rotor 34, transfer means 20, 22 and 26 are all preferably pivoting aspirators, the aspirator at transfer means 26 having dual probes 36. Transfer means 20 preferably uses disposable tips, which can be presented for pick-up on supply station 12. Additional tips 37 can be presented on turntable 38 for use by means 20 during a dilution step. On the other hand, the aspirator for transfer means 22 preferably uses a more permanent dispensing tip, which uses a wash station 40 as is conventional.

Cuvettes can be positioned for dispensing at station 14 by mounting them in, e.g., a ring 42 that moves with rotor 16, any suitable pusher 43, FIG. 2, being used to displace a cuvette from ring 42 into incubator 50 below.

Although any cuvette can be used, preferably it is a cup-like container "C", having on its inside wall surface 44 an antibody pre-attached to the wall surface. The antibody is useful in, e.g., a conventional sandwich assay which produces a complex of antibody-antigen-labeled antibody for generating a chemiluminescent signal.

The Incubator

Figure 3:
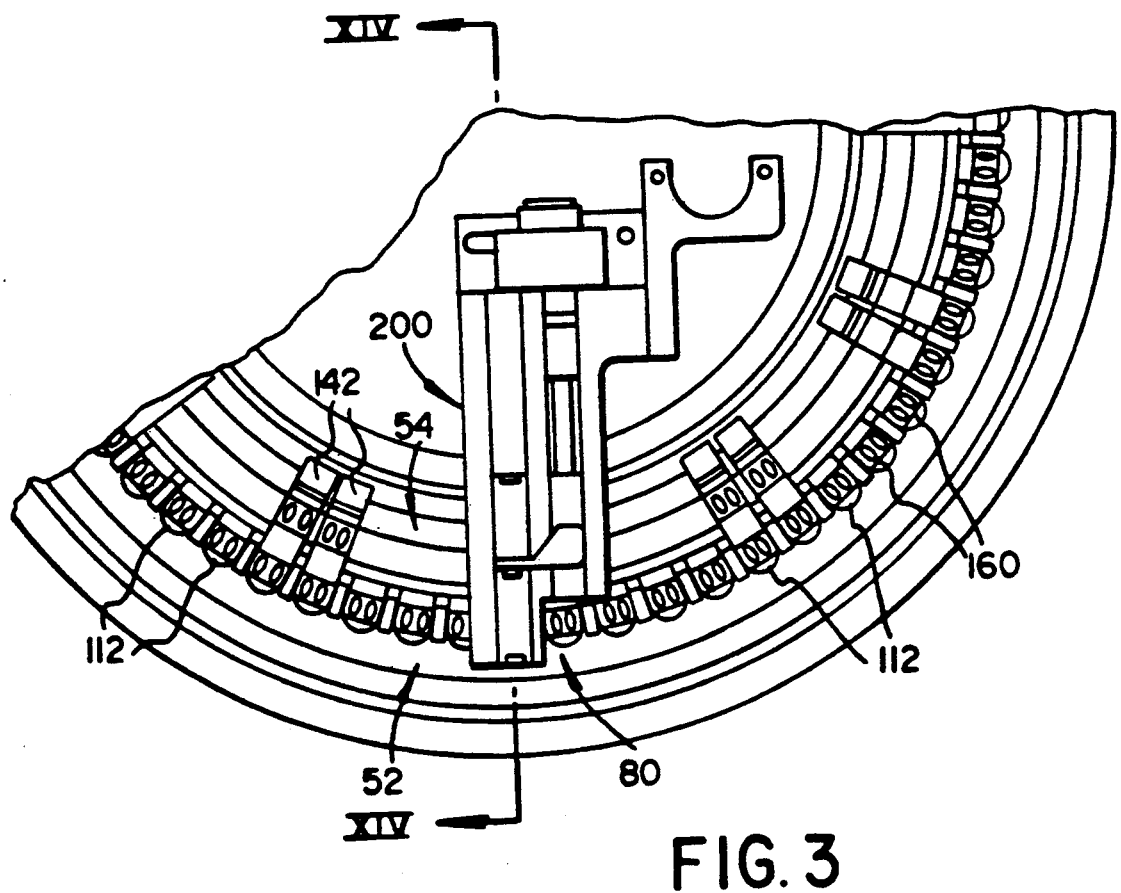
FIG. 3 is a fragmentary plan view of the incubator of FIG. 2 with the cover removed.

A preferred incubator 50 for use of the invention is described and claimed in commonly owned U.S. application Ser. No. 887,990 filed on May 22, 1992, now U.S. Pat. No. 5,244,633 by Raymond F. Jakubowicz et al, entitled "Analyzer Incubator With Plural Independently Driven Rings Supporting Cuvettes". It comprises, FIG. 2, two concentrically mounted support rings 52, 54 for receiving and carrying cuvettes C (delivered preferably first to ring 52 by any pusher means 43), rotating means for independently rotating rings 52 and 54 about a common axis 55, moving means 200 (FIG. 3) discussed hereinafter, for moving a cuvette, arrow 56 of FIG. 2, from ring 52 to 54, processing stations around the rings, and heating means to incubate the contents of the cuvettes on rings 52 and 54. Rings 52 and 54 are shown only schematically in FIG. 2 in association with the related components. Rotating means for the rings preferably comprise gear teeth 62, 64 disposed on each of rings 52 and 54, respectively, to be driven by pinion gears 66 and 68.

As noted above, various processing stations are disposed around the circumference of rings 52 and 54, in addition to an entrance port 70 for cuvettes C. They are as follows, FIGS. 1 and 2: Station 72 is permanently disposed above ring 52 and is the place where the dispensing tip 37 of aspirator 20 (not shown in FIG. 2) descends to dispense sample into a cuvette in ring 52. First reagent addition station 74 is permanently disposed at least above ring 52 so that the permanent tip of aspirator 22 can dispense at least a first reagent into a cuvette in ring 52. Optionally, aspirator 22 can also be used to dispense a second reagent, namely a conjugate reagent, as well. Second reagent addition station 76, here for signal reagent, is disposed permanently above at least inner ring 54, to descend to dispense signal reagent into a cuvette in ring 54. Wash dispensing station 78 is disposed permanently above ring 54 for washing cuvettes using wash dispenser 30. Luminometer 32 is permanently disposed above ring 54 for reading chemiluminescence. Finally, transfer means 200 (FIGS. 3 and 14-16) is disposed at station 80 to transfer cuvettes from ring 52 to ring 54, FIG. 2, arrow 56, and then from ring 54 to a dump, arrow 82, or back to ring 52 temporarily. Although not shown, reagent addition stations 74 and 76 can be constructed to bridge both rings, if desired, so as to allow the respective transfer means to supply reagent to both rings, albeit in separate sequences.

The temperature control for rings 52 and 54 comprise any conventional heating mechanism, such as heater elements (not shown) disposed in a cover plate 90, shown in phantom, and in stationary support tracks, e.g., track 100 disposed below both the rings, described hereinafter. Cover plate 90 is apertured at the processing stations, such as entrance port 70, an access port 102 for station 74, and the others not shown in the rest of the cover plate needed for stations 76, 78 and luminometer 32. Additionally, cover plate 90 is removed at groove 104 at station 80 to accommodate transfer means 200, shown hereinafter.

Figure 4:
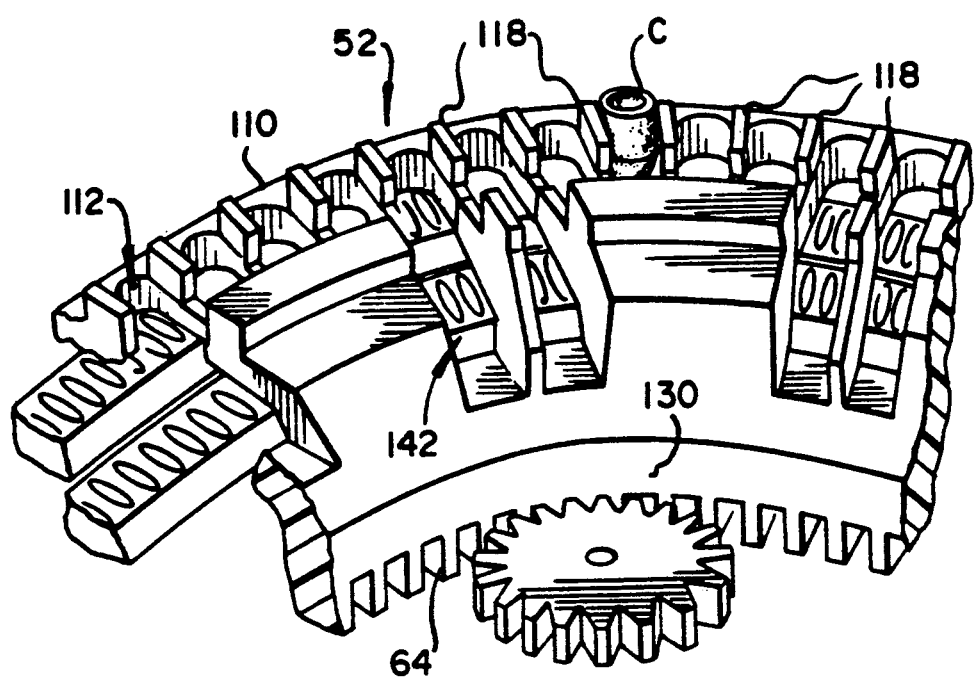
FIG. 4 is a fragmentary isometric view similar to that of FIG. 2, showing details of a segment of the incubator.
Figure 6:
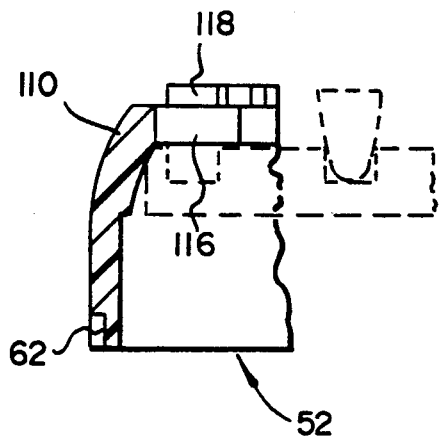
FIG. 6 is a section view taken generally along the line VI—VI of FIG. 5, showing the associated fixed frame over which a cuvette (shown in phantom) is carried.
Figure 7:
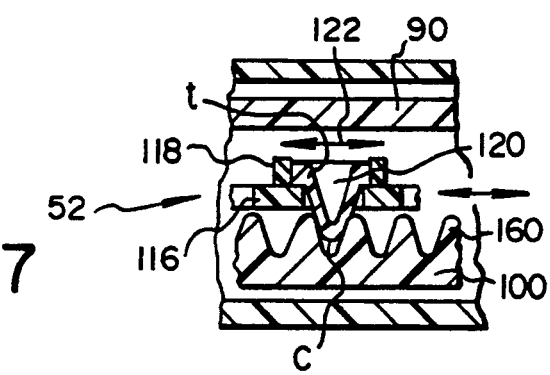
FIG. 7 is a section view taken along the line VII—VII of FIG. 5, showing the associated fixed frame over which a cuvette is carried.
Figure 5:
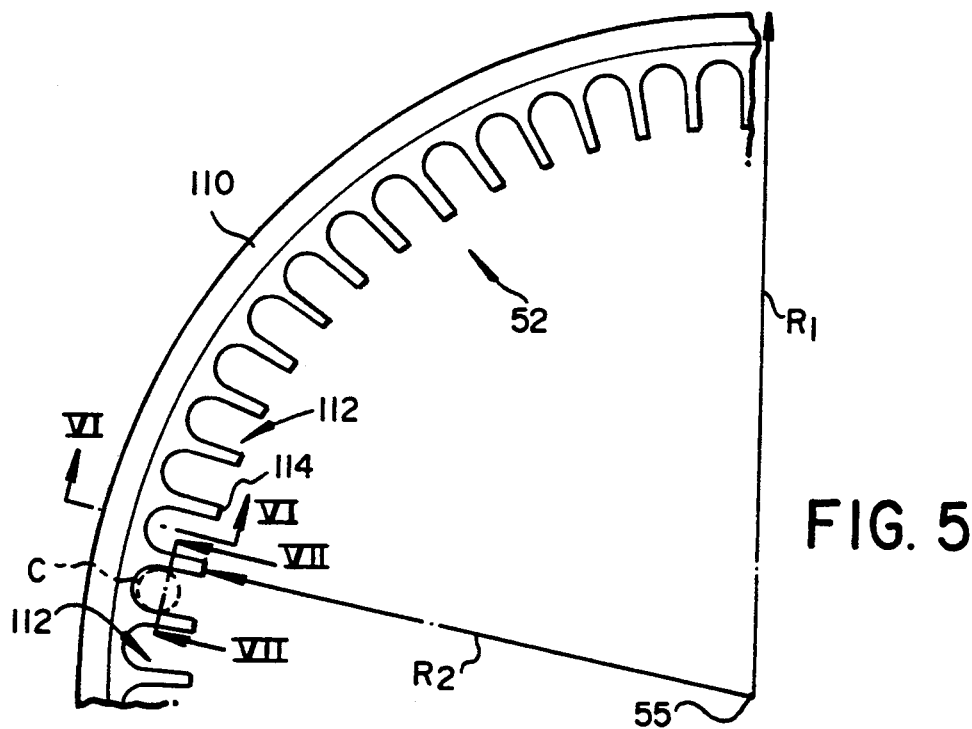
FIG. 5 is a fragmentary plan view of the outer ring of the incubator, showing one quadrant which repeats itself around the circumference of the ring.

Outer ring 52, FIGS. 3–6, preferably comprises an annulus defined principally by a continuous outer shoulder 110, FIGS. 4–6, having an outside radius $R_1$ extending from axis 55, FIG. 5. To define slots 112 for each cuvette, notches are formed in the annulus from the inside surface 114 of the annulus having an inside radius of curvature $R_2$. The notches are open towards axis 55, so that a cuvette C (in phantom) can be moved from outer ring 52 to the inner ring and back if necessary. Between each notch 112 there is a spoke fragment 116 shaped to support a cuvette C on top of ring 52, FIG. 7. Although spokes 116 can have a variety of cross-sectional shapes, preferred is one which is an upside-down T such that the top portion "t" of cuvette C is held between fixed shoulders 118 to prevent pivoting about point 120, arrow 122. (The support of the cuvette is best shown in FIG. 7.) Shoulders 118 are particularly useful if track 100 is provided with optional ribs 160, as shown, as shoulders 118 then reduce the rocking motion 122 that would otherwise be induced.

As shown in FIG. 6, gear teeth 62 preferably depend from the bottom portion of ring 52.

Figure 8:
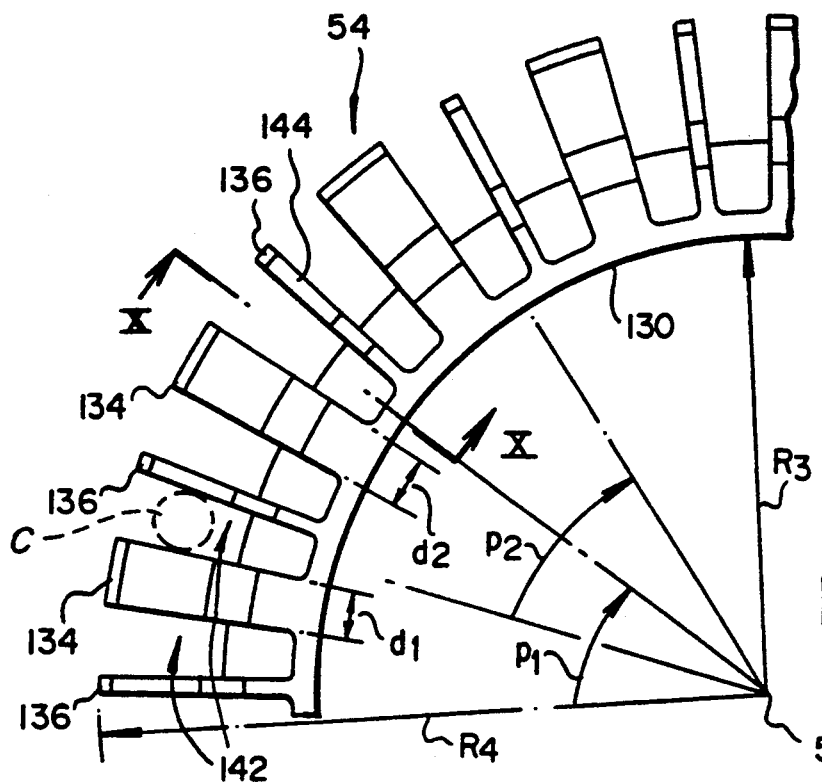
FIG. 8 is a fragmentary plan view of one quadrant of the inner ring, which quadrant repeats itself around the circumference of the ring.

Inner ring 54 comprises, FIGS. 4 and 8–9, a base annulus 130 extending completely around the circumference and having an inside radius of curvature $R_3$ measured from axis 55, FIG. 8. Mounted preferably on the inside portion of annulus 130 is a skirt with gear teeth 64, FIG. 9. Extending upward and outwardly away from annulus 130 at spaced intervals, with an outside radius $R_4$, FIG. 8, are wide flanges 134 and narrow flanges 136, spaced apart to define notches 142, each shaped to receive and carry a cuvette C (shown in phantom). Most preferably, notches 142 are in pairs with a narrow flange 136 dividing up each pair. The pitch $P_1$ between each of every other pair is controlled to match the angular spacing around the circumference of stations 76, 78 and 32. Pitch $P_2$ for the intermediate set of pairs equals pitch $P_1$, but the spacing $d_1$ and $d_2$ that positions each pair from its adjacent pair need not be equal.

Each flange 134 and 136 is shaped in cross-section as an upside down "T", similar to the spokes 116 of ring 52, FIG. 7, to provide a shoulder 144 to support upper portion "t" of the cuvette (in phantom).

Importantly, notches 142, FIG. 4, differ from notches 112 of ring 52 in that they are open in both directions, away and towards axis 55, FIGS. 4 and 8. This is needed to allow a cuvette to be moved into ring 54 from ring 52, and then into the dump, arrow 82 of FIG. 2, that is inside annulus 130.

Each of rings 52 and 54 includes flag means (not shown) that allow either a "home" position, or each cuvette position, to be sensed by a conventional sensor.

Mixing Means

Figure 10:
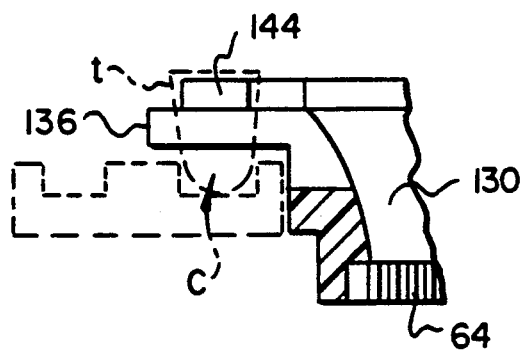
FIG. 10 is a section view taken generally along the line X—X of FIG. 8.

In accordance with the invention, mixing is preferably achieved via the surfaces that contact cuvettes "C". Included are stationary tracks 100, 100', FIGS. 11 and 12, which can have a variety of surface configurations. If cuvettes C are agitated while on rings 52 and 54 by some other surface-contact mechanism, then the top surface of tracks 100 can be smooth, except for rails 150, 152 and 154, described hereinafter. Preferably, however, the top surface of each track is provided with ribs 160, to cause cuvettes C to be agitated. More specifically, FIGS. 9 and 17, tracks 100 and 100' are provided with an outside guide rail 150 that runs along outside of the path of cuvettes C carried by ring 52, FIG. 17. Track 100' is provided with an inside guide rail 152 that runs along inside of the path of cuvettes C' carried by ring 54, and a guide rail 154 is disposed between the aforesaid two tracks and hence between rings 52 and 54. Rails 150, 152 and 154 serve to retain the cuvettes from being inadvertently displaced sideways, towards or away from axis 55. However, FIG. 10, only guide rail 150 extends completely around the circumference of track 100. Guide rail 152 is continuous except for notch 156 at station 80, so that cuvettes C', FIG. 16, can be dumped from ring 54. Guide rail 154 is the same as rail 152—it is continuous except for a notch 158 at station 80, to allow transfer of cuvettes from ring 52 to ring 54.

Figure 11:
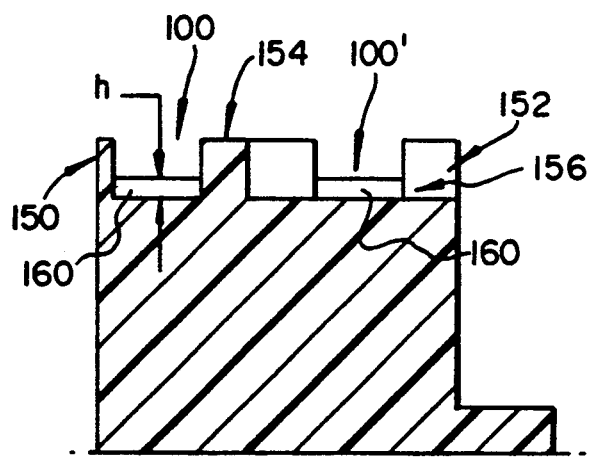
FIG. 11 is a section view taken generally along the line XI—XI of FIG. 9.
Figure 12:
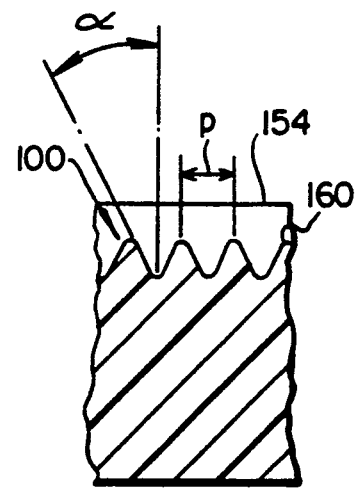
FIG. 12 is a section view taken generally along the line XII—XII of FIG. 9.

As noted above, tracks 100 and 100' between paired rails 150, 152, and 154 can be smooth, but are preferably provided with ribs 160, as are more clearly shown in FIGS. 11 and 12. The pitch "p" and height "h" are adjusted to give agitation to the contents of cuvettes C and C' to cause mixing but without spilling liquid from the cuvettes. The values of p and h depend on the rate of mixing that is desired, as well as the speed of transit over the ribs and the height of the cuvette. Further, pitch p can be different for each track, if the transit speed is different. As an example, for a rotation of between about 10 to 14 RPMs, and a cuvette height of about 12 mm, "h" can vary between about 0.6 mm and about 3.0 mm, and "p" can vary between about 1 mm and about 5.0 mm, and preferably provide a spacing that achieves a frequency of bumping that is between 20 and 165 bumps/sec., with angle alpha, FIG. 12, being between about 40 degrees and about 50 degrees. Because of restraining shoulders 118 and 144, FIGS. 7 and 8, the cuvettes are induced to "bump" over the ribs, within the confines of cover plate 90, FIG. 7. That is, cover 90 assists in preventing the cuvettes from rising too far out of their notches.

Figure 13:
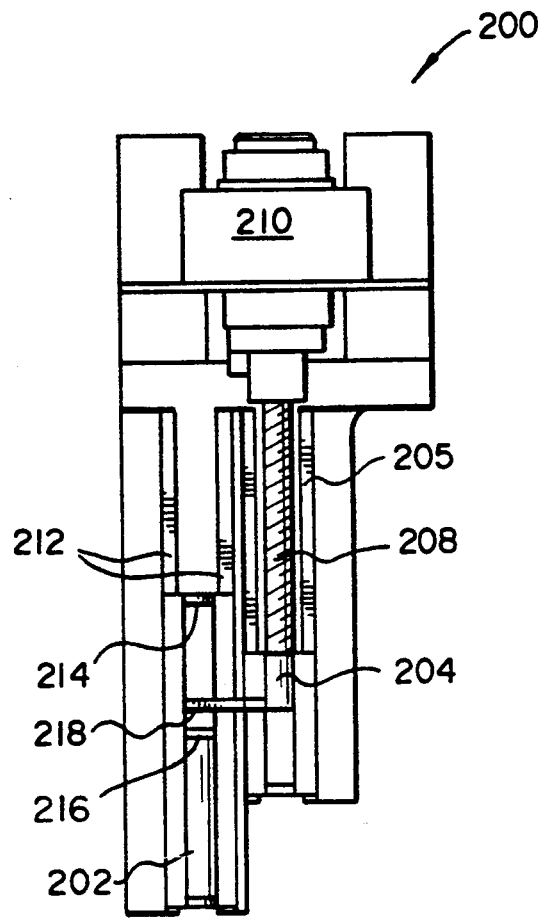
FIG. 13 is a fragmentary plan view of a shuttle useful with the invention.

Means are preferably provided for moving cuvettes from ring 52 to ring 54, and then off ring 54 out to dump. To that end, at station 80 there is provided transfer means 200, FIGS. 13–16. Such means comprise preferably a push rod 202, 204 for each of the outer and inner rings 52 and 54, respectively, mounted for transverse, reciprocal movement above their respective rings. Each rod has a terminal lip 206, FIGS. 14–16, which depends down far enough to engage any cuvette that is aligned therewith when the rod is pulled towards axis 55. To reciprocate each rod, a drive can be provided for each. Preferably, however, only rod 204 is driven (along tracks 205, FIG. 13), by reason of the rod being internally threaded to engage a lead screw 208 driven by stepper motor 210. Rod 202, on the other hand, is a follower rod that is slidably and freely mounted on track 212, with tabs 214 and 216 rising therefrom, FIGS. 14–16, to be engaged by a collar 218 on rod 204 that encircles rod 202.

Figure 14:
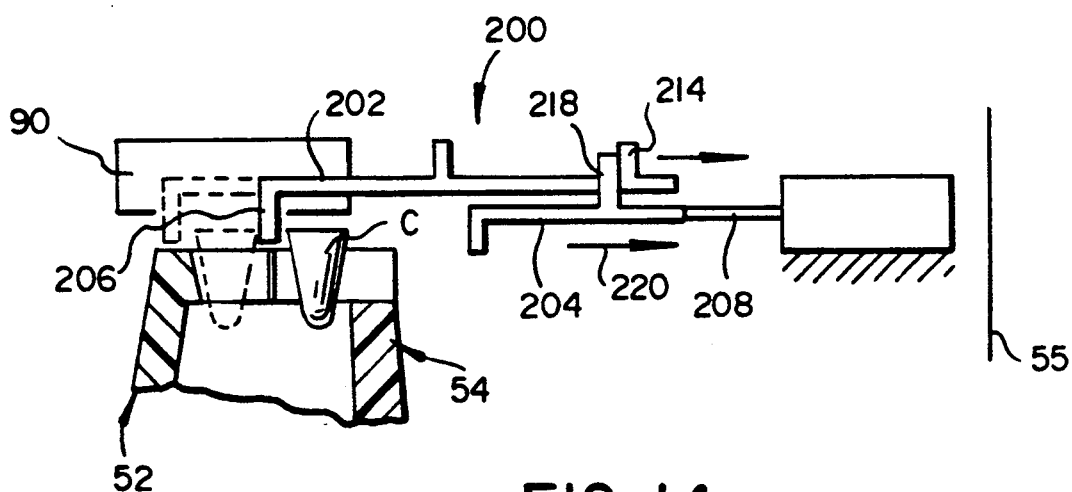
FIGS. 14–16 are fragmentary elevational views in section, showing the shuttle mechanism as it moves the cuvettes from one ring to another and then out of the incubator.
Figure 15:
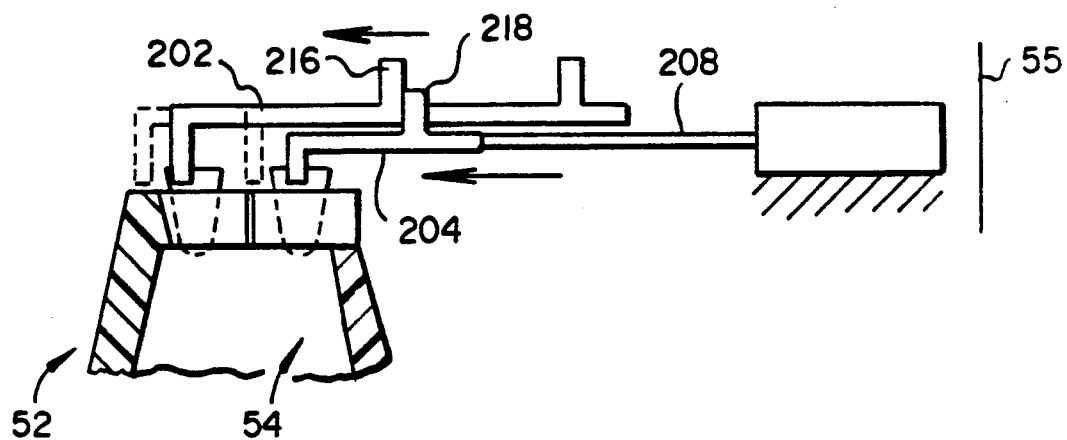
Figure 16:
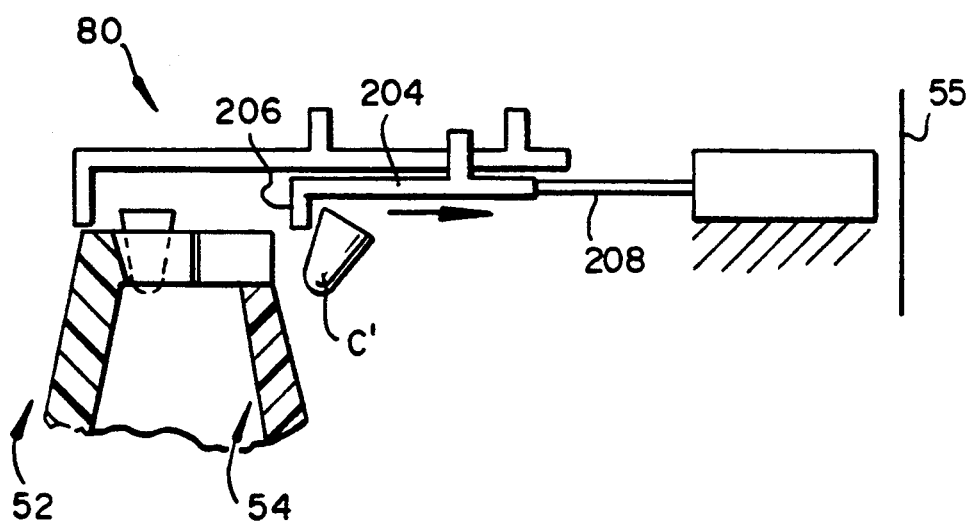

The operation of transfer means 200 will be readily apparent from the preceding. As shown in FIGS. 14–16, when a cuvette shown in phantom needs to be transferred at station 80 from ring 52 to ring 54, push rod 204 is drawn back, arrow 220, by lead screw 208, until collar 218 engages tab 214. This causes rod 202 to also traverse towards axis 55, from its phantom position, causing lip 206 thereof to move cuvette C to its solid position on ring 54. The next part of the cycle of movement, FIG. 15, is to move both rods to the outside of their respective rings, and this is done by advancing lead screw 208 and rod 204 away from axis 55 until collar 218 presses against tab 216 and pushes out rod 202 as well, from its solid position to that shown in phantom (between spaces occupied by cuvettes).

The last part of the cycle of movement is that used to transfer a cuvette C′ from ring 54 to dump, FIG. 16, at station 80. Lead screw 208 simply withdraws enough to cause lip 206 of rod 204 to pull cuvette C′ off ring 54.

It will be understood that one of the notches 142 is maintained empty of cuvettes to provide clearance for movement of lip 206 between rings.

Alternatively, in some assays the cuvette is transferred back to outer ring 52 for further reagent addition and incubation, before returning to ring 54 for washing and reading.

In addition to heated cover 90 and stationary tracks 100, 100′, additional insulative enclosures are preferably provided, FIG. 17, to retain the heat for incubation by incubator 50. That is, a housing 300 is mounted on a base 302 of an insulative material, with suitable apertures 304 positioned for access to the incubator. Those apertures are generally aligned with the apertures of cover 90, FIG. 2. Most preferably, apertures 304 are removably covered by doors 310, which can be operated by any suitable means, such as a cam 312 driven by motor 314 to engage cam followers 316 on the doors, as is more fully described and claimed in commonly owned U.S. application Ser. No. 887,976 filed on May 22, 1992 by Johannes J. Porte, and entitled "Cam-Operated Doors For An Incubator" (Doc. 63648). Most preferably, drive shaft 320 of motor 314 is on axis 55, FIG. 17.

The actual control of the temperature within incubator 50 is variable, depending on the reactions desired. Most preferably, the temperature of outer ring 52 is preferably kept within 0.5° C. of the desired temperature, e.g., of 37°, as most of the incubation occurs while on this ring. Inner ring 54, on the other hand, can be within 2° C. of the desired target temperature, but most preferably ±0.5° C.

The timing sequence for the operation of the incubator will of course depend upon a large variety of factors, including a) the angular position of each processing station about the rings of the incubator, and b) the chemistry of the immunoassays in question, as will be readily apparent.

A representative timing diagram is given in FIG. 18A and B. In this diagram, it is assumed that reagent transfer means 22 goes to reagent supply station 16, FIG. 1, twice for two different reagents. The first 15 functions are defined as operations pertaining to outer ring 52, whereas the remainder are for inner ring 54.

Considering the overall operation of the incubator, it proceeds as follows, under the control of conventional computing means (not shown). ("Step" numerals appear in parentheses in FIGS. 18A and B, and "SGR" is an abbreviation for "signal reagent".)

Step 1: a cuvette C is dropped into a notch in outer ring 52.

Step 2: ring 52 is rotated to move that cuvette into position at station 72 (FIG. 2) to receive a sample liquid.

Step 3: sample is dispensed at station 72.

Step 4: ring 52 is rotated to move the cuvette to reagent addition station 74 (FIG. 2).

Step 5: reagent is dispensed at station 74 using transfer means 22.

Step 5′: rotate ring 52 to allow other operations on other cuvettes, while incubating and agitating this cuvette.

Step 6: rotate ring 52 to move it back to station 74 for optional conjugate reagent addition.

Step 7: dispense second reagent, if needed.

Step 8: (not labeled on FIG. 18): incubate and agitate for a minimum of 15 minutes.

Step 9: rotate ring 52 (and ring 54) to place cuvette at station 80.

Step 10: activate transfer means 200 to move cuvette from ring 52 to ring 54.

Step 11: align cuvette on ring 54 at station 78 for washing of the cuvette.

Step 12: wash cuvette at station 78.

Step 13: repeat alignment step 11 until cuvette is at station 76.

Step 14: dispense signal reagent at station 76.

Step 15: repeat alignment step 11 until cuvette is at read station 32.

Step 16: read cuvette with the luminometer.

Step 17: repeat step 11 until cuvette is at station 80.

Step 18: activate push rod 204 to dump the cuvette.

In the aforedescribed sequence, ribs 160 are included in the portion of track 100 that is to be used for mixing, e.g., of a diluent added to a sample.

It is not essential that the mixing protrusions be precisely as shown in FIGS. 11 and 12. Instead they can have different configurations, as shown in FIGS. 19–22. Parts similar to those previously described bear the same reference numerals, to which the distinguishing suffixes A–D, respectively, are added. In all these, a stationary track 100A, 100B, 100C or 100D supports the ribs.

Figure 19:
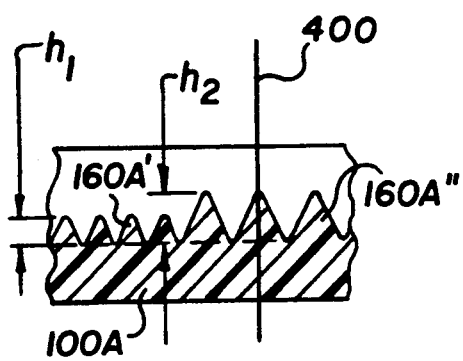
FIGS. 19 and 20 are section views similar to FIG. 12, but of alternate embodiments of the protrusions.

Hence, FIG. 19, ribs 160A are of varying height, e.g., 160A′ and 160A″, depending on whether less vigorous or more vigorous mixing, respectively, is desired. For example, $h_1$, can be about 0.6 mm, and $h_2$ about 3.0 mm. In all cases, the ribs 160A are generally normal to track 100A, as noted by axis "400".

Figure 20:
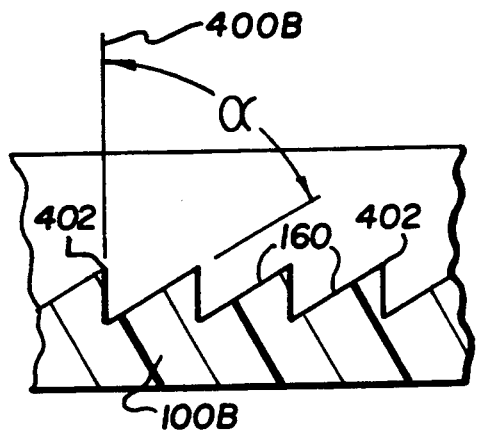
Figure 21:
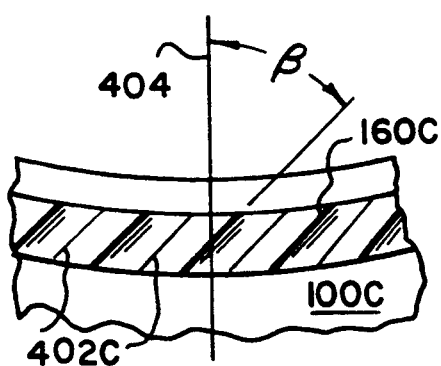
FIG. 21 is a fragmentary plan view of the stationary track, showing still another embodiment.
Figure 22:
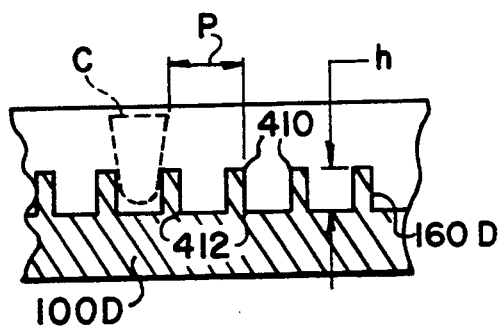
FIG. 22 is a section view similar to that of FIG. 19, but of yet another embodiment.

However, FIG. 20, ribs 160B need not be normal to track 100B, but can be sawtoothed, with an angle alpha from the "normal" 400B which can be from about 5 to about 85°.

In all the previous embodiments, the ribs have a radial extension on the track—that is, edges 402, FIG. 20, of the ribs are aligned with a radius of the track, which itself is generally circular in plan view. However, such radial alignment is far from being essential. Edges 402C of ribs 160C, FIG. 21, can deviate from the radial extension 404 by angle "beta" which can be from 0° to about 85°, to also provide a rotational movement of the well.

In yet another embodiment, it is not necessary that the ribs have smooth surfaces with no sharp corners. Instead, FIG. 22, ribs 160D have sharp exterior corners 410, and optionally sharp interior corners 412 where the ribs join track 100D. The values of "p" and "h" can be as described above.

Figure 23:
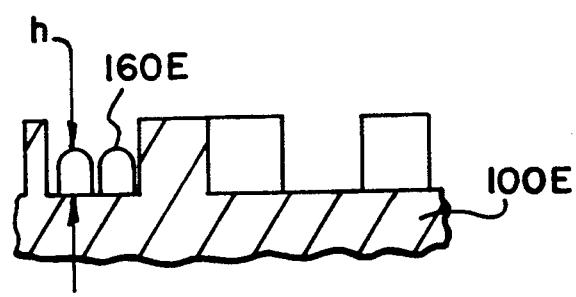
FIG. 23 is a section view similar to that of FIG. 11, but again of still another embodiment of the protrusions.

Alternatively, the ribs need not extend all the way across their track, FIG. 23. Parts similar to those previously described bear the same reference numeral to which the distinguishing suffix "E" is appended. Thus, track 100E is constructed and used in an analyzer like all the previous embodiments, except that ribs 160E are each a pair of teeth protruding upward, FIG. 23, with any of the shapes, sizes "h" and pitches "p" described above. The teeth can be staggered or aligned.

Figure 24:
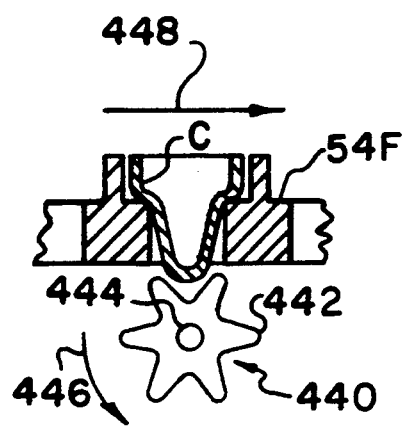
FIGS. 24 and 25 are fragmentary elevational views in section of still additional alternate embodiments of the mixing means of the invention.

Still further, there is no need for the mixing means to be fixed to a stationery track. Instead, they can be part of a rotating member that rotates against a cuvette carried by the rings above, FIG. 24. Parts similar to those previously described bear the same reference numbers, to which the distinguishing suffix "F" is appended. Thus, FIG. 24, the analyzer is the same as for previous embodiments, except there are no ribs fixed to a track below ring 52F or 54F (only 54F being shown). Rather, a pinion 440 having teeth 442 of judiciously-chosen shapes and sizes is driven on a shaft 444, preferably in a direction 446 that is counter to the movement 448 of ring 54F during mixing. Directions 446 and 448 can then be reversed if repeated passage of cuvette C over pinion 440 is desired.

Likewise, it is not necessary that the mixing means be mounted to project vertically up to the rings carrying the cuvettes. Instead, the protrusions can be ribs projecting from the side of the stationary track, FIGS. 25 and 26. Parts similar to those previously described bear the same reference numeral, to which the distinguishing suffix "G" is appended.

Figure 25:
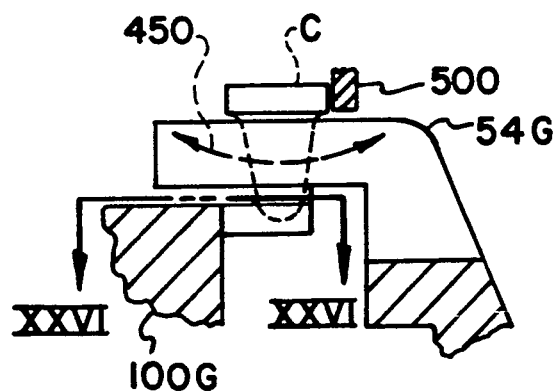
Figure 26:
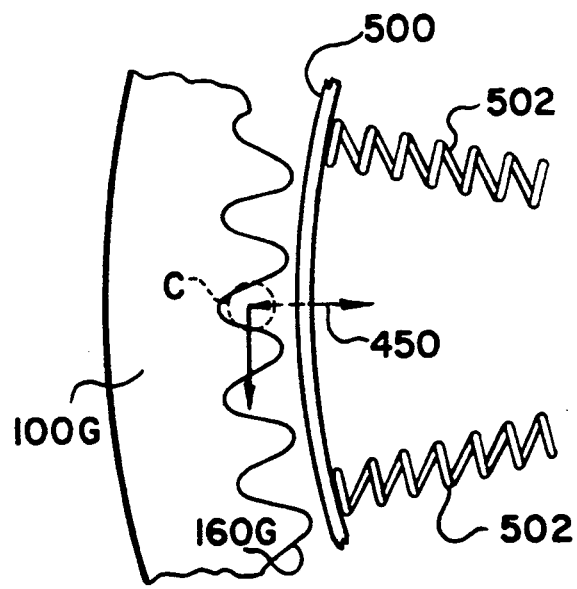
FIG. 26 is a section view taken generally along the line XXVI—XXVI of FIG. 25.

Thus, ring 54G carries cuvette C, FIG. 25, in the same manner as in previous embodiments. However, track 100G has its ribs 160G in the form of sideways-projecting teeth, FIG. 26, here shown with a sinusoidal shape as in the embodiment of FIGS. 11 and 12. These cause cuvette C to jerk inward and outward, arrow 450. A compliant ring 500, using biasing springs 502, FIG. 26, can be used to keep cuvette C in contact with ribs 160G.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. In an analyzer for conducting a wet assay in a liquid in a cuvette, the analyzer comprising first station means for adding a liquid reagent to liquid in a cuvette, second station means for mixing the reagent with the liquid already in the cuvette, and station-to-station means for moving cuvettes from station-to-station along a path, said means for mixing comprising at least one set of spaced-apart protrusions projecting out into said path traced by the cuvette, said means for moving cuvettes from station-to-station along a path providing relative motion between said protrusions and at least one of said cuvettes, so that at least one said cuvette is repeatedly disturbed by being placed in direct contact with said projecting protrusions and the liquid content to be mixed;

the improvement wherein the total volume of liquid to be mixed is no greater than about 200 μl, and said protrusions create a bump frequency of about 20 to about 165 bumps per second and a bump amplitude, measured as the amount of vertical displacement of the bottom of said cuvettes of between about 0.6 and 3.0 mm.

2. An analyzer as defined in claim 1, wherein said protrusions are fixedly attached in an array under said path, and wherein said station-to-station means and said relative-moving means comprise the same means for moving cuvettes over said array of protrusions.

3. An analyzer as defined in claim 2, wherein said protrusions comprise regularly-spaced ribs of a height and spacing effective to cause complete mixing of the liquids, but not expulsion of the liquids from the cuvettes.

4. An analyzer as defined in claim 1, wherein said protrusions are mounted on a cam wheel and said relative-moving means comprise means for rotating said wheel independently of said station-to-station means.

5. An analyzer as defined in claims 1 or 2, wherein said protrusions comprise ribs on a fixed frame and only a portion of said frame under said cuvette path is occupied by said ribs, the remainder of said frame being free of obstructions to allow movement of cuvettes into and out of said support without contact with obstructions on said frame.

6. An analyzer as defined in claim 5, wherein said ribs where present are of a uniform height and spacing.

7. An analyzer according to claim 1 or 2, wherein said station-to-station moving means comprise a first annular support apertured to receive and support cuvettes, and moving means for moving the first support and its cuvettes along a first path defined by a first annular ring, said protrusions being arranged to lie in a complimentary annular ring, portions of which are free of protrusions.

8. An analyzer according to claim 7, wherein said station-to-station moving means further include a second annular support apertured to receive and support cuvettes and which is arranged to be adjacent the first annular support, and moving means for moving the second support and its cuvettes along a second path defined by a second annular ring, a second set of spaced-apart protrusions being provided in the second path under the second support to effect mixing of the liquid contained in the cuvettes carried by the second support.

9. An analyzer as defined in claim 8, wherein both of said supports, said paths of movements, and said sets of protrusions, comprise or are fixed in an annular ring.

10. An analyzer as defined in claim 8, wherein said fixed array of said second protrusions does not completely occupy the space below the path of movement of cuvettes carried by said second support and the space unoccupied by said second set of protrusions is functionally aligned in at least one location with said portion of said annular ring of said frame for said first protrusions, so that a cuvette can be moved at said one location between said supports without contact with obstructions on said frame.

* * * * *